United States Patent [19]

Takahashi

[11] Patent Number: 4,867,170
[45] Date of Patent: Sep. 19, 1989

[54] MEASURING APPARATUS FOR BLOOD PRESSURE

[75] Inventor: Masakatsu Takahashi, Ashiya, Japan

[73] Assignee: Kabuskiki Kaisha Hi Bridge, Osaka, Japan

[21] Appl. No.: 179,337

[22] Filed: Apr. 8, 1988

[30] Foreign Application Priority Data

Jul. 3, 1987 [JP] Japan .............................. 62-167447

[51] Int. Cl.⁴ .............................................. A61B 5/02
[52] U.S. Cl. .................................... 128/677; 128/690
[58] Field of Search ......................... 128/672, 677–690

[56] References Cited

U.S. PATENT DOCUMENTS

| | | |
|---|---|---|
| 2,753,863 | 7/1956 | Bailey . |
| 2,799,270 | 7/1957 | Rodbard . |
| 2,833,274 | 5/1958 | Reiss . |
| 3,032,030 | 1/1982 | Han . |
| 3,299,882 | 1/1967 | Masino ............................. 128/687 X |
| 3,391,691 | 7/1968 | Young ................................. 128/678 |
| 3,535,067 | 10/1970 | Lesher et al. ........................ 128/672 |
| 3,704,708 | 12/1972 | Iberall . |
| 3,880,145 | 4/1975 | Blick .................................... 128/672 |
| 4,116,217 | 9/1978 | Speidel . |
| 4,127,114 | 11/1978 | Bretscher . |
| 4,331,154 | 5/1982 | Broadwater et al. ............... 128/677 |
| 4,561,447 | 12/1985 | Kawamura et al. ................ 128/687 |
| 4,660,566 | 4/1987 | Palti . |

FOREIGN PATENT DOCUMENTS

| | | | |
|---|---|---|---|
| 3030566 | 3/1982 | Fed. Rep. of Germany ...... | 128/672 |
| 0616801 | 4/1980 | Switzerland ......................... | 128/672 |
| 2180944 | 4/1987 | United Kingdom ................ | 128/672 |

Primary Examiner—Angela D. Sykes
Attorney, Agent, or Firm—Armstrong, Nikaido, Marmelstein, Kubovcik & Murray

[57] ABSTRACT

A measuring apparatus for blood pressure comprises a blood pressure measuring portion and a holder pipe. The blood pressure measuring portion comprises a device for searching a location of an artery appropriate for blood pressure measurement and for detecting a pulse by being pressed on a skin surface above or near the artery. A device is provided for detecting blood pressure, a device for blocking blood stream, a portion for indicating a measured value of blood pressure and a portion for indicating a detected pulse of the artery appropriate for measurement are also provided. The blood pressure measuring portion is inserted slidably in the holder pipe. The holder pipe is equipped removably with a strap for fixing the holder pipe.

13 Claims, 6 Drawing Sheets

MEASURING APPARATUS FOR BLOOD PRESSURE

FIELD OF THE INVENTION

The present invention relates to an apparatus for measurement of blood pressure, and more particularly to an apparatus capable of detecting blood pressure of palpable small arteries at any region on the human body by pressing a point on the artery.

BACKGROUND OF THE INVENTION

Measurement of blood pressure, in general at a hospital and the like, plays an important role in a medical examination of the human body. Therefore, it usually is carried out at the beginning of medical examinations. Recently, blood pressure measurement using a sphygmomanometer for domestic use available in the market is popular among even healthy persons, so that a change in blood pressure is checked at any time for monitoring the condition of health.

Systolic blood pressure of a young healthy person is maintained at around 120 mmHg, and diastolic blood pressure at around 70 mmHg, and the integrity of the blood vessel wall is maintained so that the blood vessel can cope with any change of environment.

However, in case of some types of diseases and in some aged persons, the integrity of the blood vessel wall is lost and like an old rubber tube. Therefore, the blood vessel cannot tolerate an increased blood pressure caused by changes of the environment, physical condition, atmospheric temperature, strain in the body and mind or the like, and accordingly, there is a danger which can result in a rupture of the blood vessel wall.

An apparatus for measurement of blood pressure used widely at a hospital and the like today consists of a rubber bladder (called "manchette") which is wound around the upper arm and a detector for Korotkoff sounds. In the measurement using this kind of apparatus, first the brachial artery is blocked by increasing pressure of the rubber bladder with air using an air charging apparatus. Second, the air pressure in the rubber bladder is gradually lowered. Korotkoff sounds generated by intermittent jet flow of blood are monitored. The maximum (systolic) blood pressure and the minimum (diastolic) blood pressure are determined by checking the cuff pressure with the gauge indication in case of a Tycos type sphygmomanometer having an analog indication or by checking with indication sounds or indication lights and a reading of a pressure indicator in case of a sphygmomanometer having a digital indication.

In measurements using the above conventional apparatus, a region for measurement is restricted to an upper arm, and movement of the human body is also restricted. Further, the above conventional apparatus is too bulky to carry, therefore the conventional apparatus is not suitable for being carried with a healthy person for easy measurement of blood pressure at any convenient time during daily activities or on a journey.

The present invention was made considering the above mentioned problems of the conventional apparatus for blood pressure measurement.

It is an object of the present invention to provide a measuring apparatus for blood pressure which enables us to correctly search a location of an artery appropriate for measurement and to correctly measure blood pressure at the measuring point at any time. Because of a small size, it enables us to carry out easy measurement of blood pressure at any region of a human body. Frequent measurements during free activities of the body are important to prevent apoplexy.

SUMMARY OF THE INVENTION

The above object is attained and the problem is solved by the present invention which relates to a measuring apparatus for blood pressure comprising a blood pressure measuring portion and a holder pipe, wherein the blood pressure measuring portion comprises a device for searching a location of an artery appropriate for blood pressure movement and for detecting a pulse by being pressed on a skin surface above or near the artery, a device for detecting pressure, a device for blocking the blood stream, a portion for indicating a measured value of blood pressure and a portion for indicating a detected pulse of an artery appropriate for measurement. The blood pressure measuring portion is mounted slidably on the holder pipe, and the holder pipe is equipped removably with a strap for fixing the holder pipe.

When a blood pressure measurement is carried out at an arm using a measuring apparatus having the above mentioned construction, a skin surface above or near any artery is pressed by the device for searching a location of an artery and for detecting the pulse. Then the location of the artery, appropriate for measurement, is determined for the detected pulse.

Thereafter, the holder pipe holding the blood pressure measuring portion is fixed to the arm at the decided position by means of the strap, in order to prevent slippage. The blood pressure measuring portion is pressed by a finger to slide downward in the holder pipe. The lower end of the blood pressure measuring portion presses the skin surface strongly. Thereby, the artery for measurement is pressed and blocked by the blood stream blocking means provided on the blood pressure measuring portion. Thereafter, the blood pressure measuring portion is gradually slid upward in the holder pipe due to the restitution force of the blood stream blocking device and the constriction of the artery is gradually released. By carrying out the above mentioned series of operation, the maximum blood pressure and the minimum blood pressure are detected by the pressure detecting device. The pulse rate can be known and information as to whether or not the pulse is arrhythmic can also be known at the time between the miximum blood pressure and the minimum blood pressure detection, namely during the period for the indication of the pulse pressure. The detected values are indicated on the portion for indicating the measured blood pressure value.

It is desirable that the measurement is carried out by a user whose measuring point is kept at the level of his heart.

When a blood pressure measurement is carried out at a region of the human body other than an arm using an measuring apparatus for blood pressure of the present invention, a strap is removed from the holder pipe and a blood pressure measuring portion is pressed on the region for measurement with the holder pipe being used as a guide. Then, blood pressure is measured in a manner similar to that described above.

DETAILED DESCRIPTION

Referring now to the drawings for more complete understanding of the invention, there is explained in detail an embodiment of the present invention.

Figure 1:
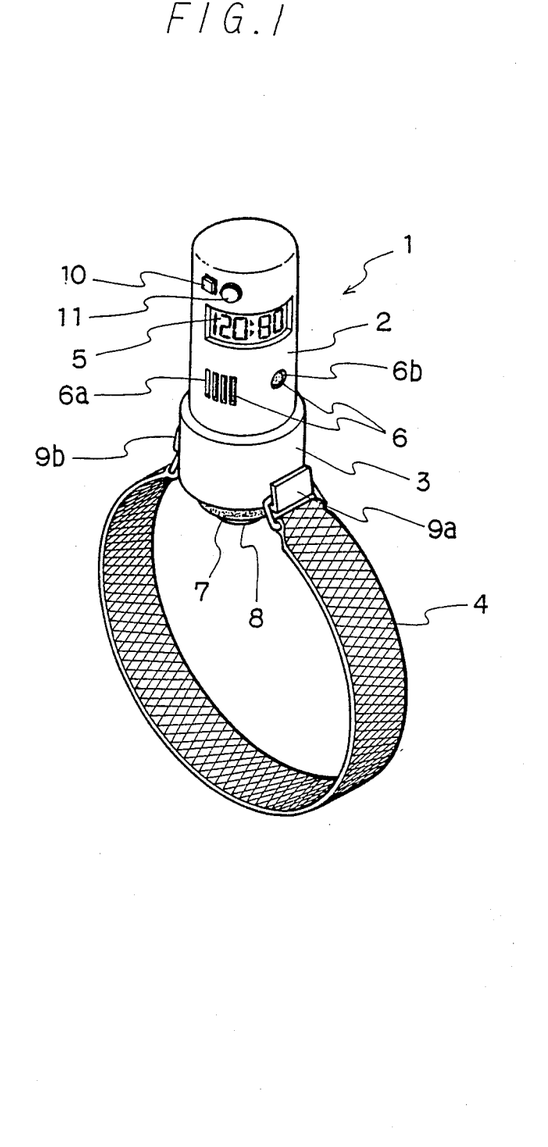
FIG. 1 is a perspective view showing an embodiment of an apparatus of the present invention which has a digital-type indication portion.
Figure 2:
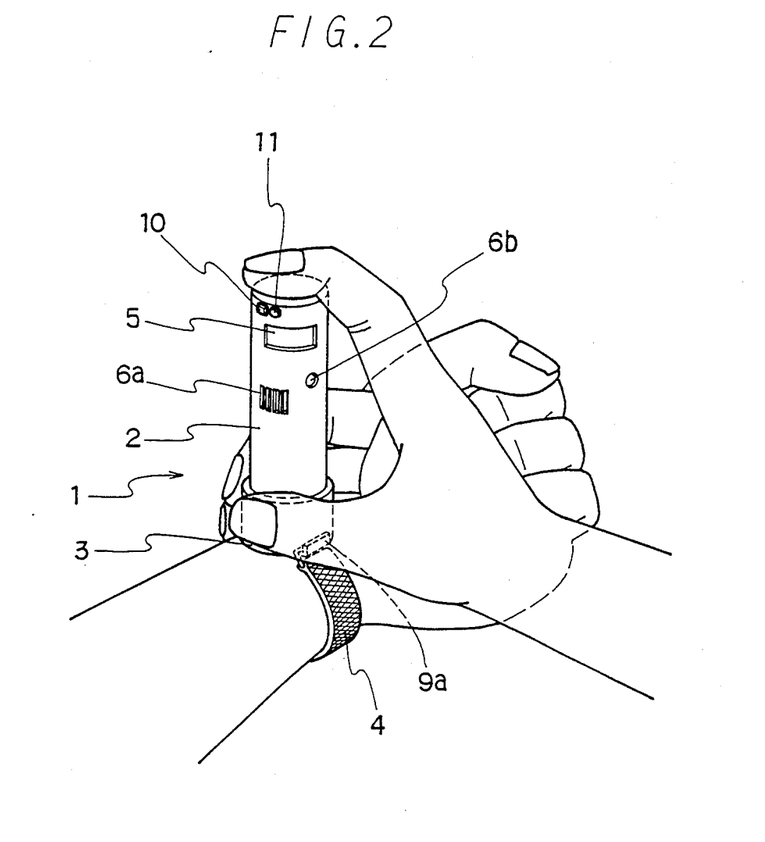
FIG. 2 is a perspective view showing a usage of an apparatus of the present invention employed for measuring blood pressure on an arm.

FIGS. 1 to 2 show a blood pressure measuring apparatus 1 of the present invention which has a digital-type indicating portion, wherein the apparatus 1 comprises a blood pressure measuring portion 2, a holder pipe 3 which slidably supports the portion 2, and a strap 4 attached to the holder pipe 3.

In this embodiment of the invention, the blood pressure measuring portion 2 is formed in a cylindrical shape comprising a means for searching a location of an artery appropriate for blood pressure measurement and for detecting a pulse by being pressed on a skin surface above or near an artery, a blood stream blocking means for constricting the artery for measurement, a pressure detecting means for detecting the maximum blood pressure and the minimum blood pressure, a portion 5 for indicating a measured value of blood pressure and a portion 6 for indicating a detected pulse of an artery appropriate for measurement.

As a means for searching a location of an artery appropriate for blood pressure measurement and for detecting a pulse, there is provided a pulse sensor 8 placed on the outer surface of an elastic portion 7 located at the lower end of the blood pressure measuring portion 2. A pressure sensor and a detecting circuit for pulse/Korotkoff sounds are mounted in the blood pressure measuring portion 2. A change-over switch 11 to change from the pulse sensor 8, used for searching a location of the artery appropriate for blood pressure measurement, to the pressure sensor used for detecting Korotkoff sounds and vice versa is located on the upper part of the blood pressure measuring portion 2.

The detecting circuit for pulse/Korotkoff sounds provided inside of the measuring portion 2 is connected to the portion 5 for indicating a measured value of blood pressure and to the portion 6 for indicating a detected pulse of an artery appropriate for measurement which are provided on the upper part of the measuring portion 2. The portion 6 for indicating a detected pulse of an artery appropriate for measurement comprises an indication lamp 6a and an electronic tone generator 6a, wherein the indication lamp 6a flickers in accordance with the pulse detected, and the brightness of the lamp is changeable in accordance with intensity of the pulsation. In addition, the electronic tone generator 6a utters a special electronic tone with the assistance of the detecting circuit for pulse/Korotkoff sounds at a moment when Korotkoff sounds are detected by the pressure sensor and at a moment when they disappear. It is a matter of course that the circuit can be designed to continuously utter sounds during the period from the appearance to the disappearance of Korotkoff sounds. Further the portion 5 for indicating a measured value of blood pressure is designed to indicate the maximum and the minimum blood pressure in digital form in an instant. A pressure sensor provided inside of the blood pressure measuring portion 2 detects the change of the internal air pressure of the elastic portion 7 due to the deformation thereof and the maximum blood pressure and the minimum blood pressure are indicated on the measured value indicating portion 5 in digital form via the pressure detecting circuit provided in the blood pressure measuring portion 2. The type of the measured value indicating portion 5 is not limited to a digital-type, and another type, for example analog-type, can be employed. The numeral 10 denotes a power switch.

Moreover, in the present embodiment the elastic portion 7 located at the blood pressure measuring portion 2 is made of rubber having restitution force formed into a shape of a hemispheric shell whose diameter or diagonal length is normally not larger than 10 mm. It is a matter of course that in accordance with the size of an artery appropriate for blood pressure measurement, the diameter or diagonal length of the rubber hemispheric shell can be equal to, or larger than, or smaller than the diameter of the artery, i.e. the rubber shell can be an extra large one or an extra small one. In addition, the rubber hemispheric shell can be in such a size that the end of the blood pressure measuring portion 2 is covered with the rubber hemispheric shell. The elastic portion 7 can be replaced freely by another one when it degrades or loses the restitution force.

Further, the material of the elastic portion 7 is not limited to rubber. Any other restorable material which makes the blood pressure measuring portion 2 gradually slide upward along the inner surface of the holder pipe 3 by means of the resilient restitution force can be adopted. It is particularly preferable to select a material which does not easily degrade or does not easily lose the restitution force.

Figure 5A:
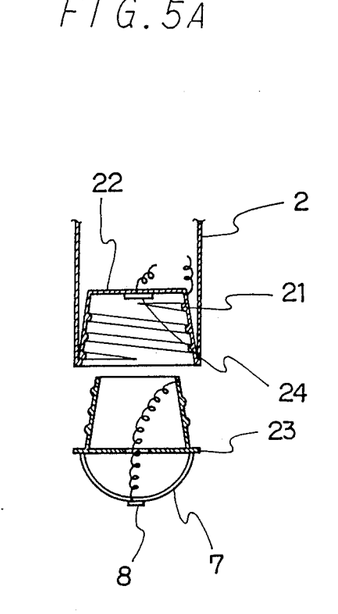
FIGS. 5A to 5C are sectional views showing constructions for mounting the elastic portion.
Figure 5B:
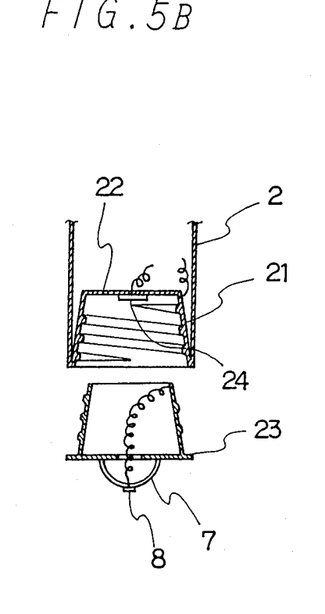
Figure 5C:
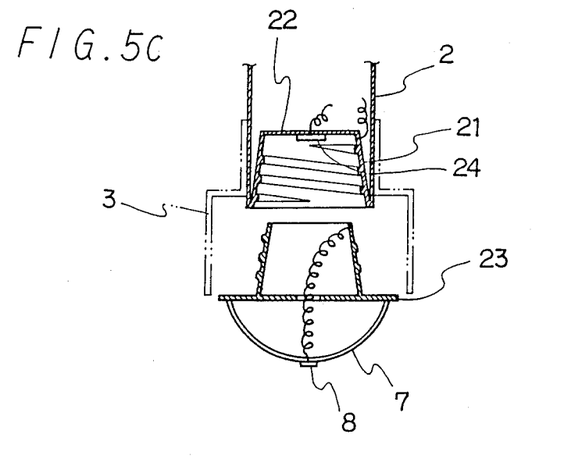

Example constructions for mounting the elastic portion 7 are shown in FIGS. 5A to 5C. There provided an inner side wall 21 and a ceiling wall 22 in the blood pressure measuring portion 2. The elastic portion 7 is fixed to a coupling 23 which can be connected to the inner wall 21, and the coupling 23 and the inner wall 21 form an air-tight seal, for example, a flat type seal, a screw type seal, a combined type seal of the flat type and the screw type and the like. Several couplings having differently sized elastic portions can be prepared so that the elastic portion having a desirable size can be selected among them and can be mounted on the bottom of the blood pressure measuring portion 2. The pressure sensor 24 for detecting air pressure and Korotkoff sounds is provided on the surface of the ceiling wall 22 and the pulse sensor 8 is provided on the surface of the elastic portion 7.

The blood pressure measuring portion 2 having the above mentioned construction is slidably mounted on the holder pipe 3.

Namely, the end of the blood pressure measuring portion 2 at which the elastic portion 7 is provided is slidably inserted into the holder pipe 3, so that the blood pressure measuring portion 2 can be slid down along the inner surface of the holder pipe 3 when the top of the measuring portion 2 is depressed by a finger. When the top of the measuring portion 2 is released by the finger, the measuring portion 2 gradually slides upward along the inner surface of the holder pipe 3 by elastic recoil of the compressed elastic portion 7 on the skin surface.

Further, two engaging portions 9a, 9b for engaging with the strap are provided on the outside of the holder pipe 3 in such a manner that the engaging portions 9a, 9b are opposed to each other. The strap 4, which includes elastic material such as rubber and can stretch, is removably engaged to the engaging portions 9a 9b. It is a matter of course that one end of the strap 4 can be made free while the other end is engaged with one of the engaging portions 9a, 9b of the holder pipe 3. In addition, the strap 4 can be made of leather, cloth or other materials.

Figure 6:
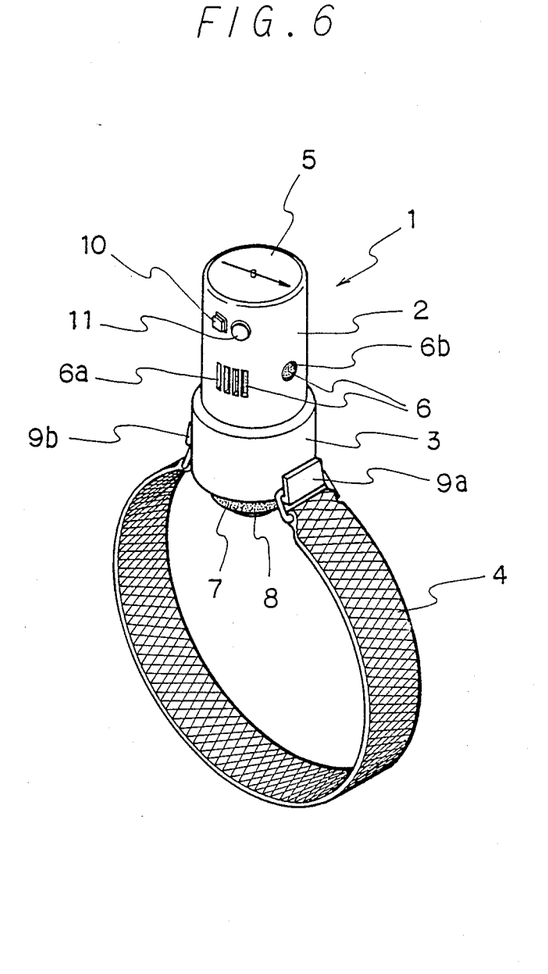
FIG. 6 is a perspective view showing another embodiment of an apparatus of the present invention which has an analog-type indication portion.

FIG. 6 shows another embodiment of an apparatus of the present invention which has an analog-type indicating portion. In FIG. 6, the same numeral as the corresponding part in FIG. 1 is used for each part. The embodiment is FIG. 6 has the same construction as that in FIG. 1 excepting that the type of the portion for indicating a measured value of blood pressure is different.

Figure 3A:
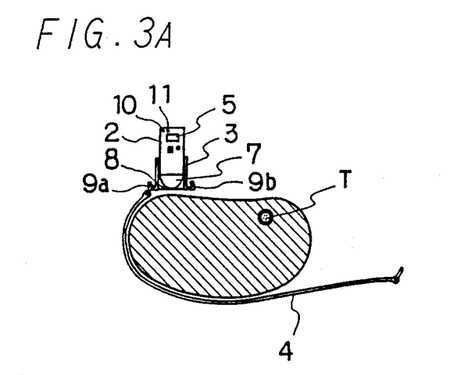
FIGS. 3A to 3E are explanatory views showing the procedure for measuring blood pressure by an apparatus of the present invention.

Next, there is explained an example usage of the measuring apparatus 1 described above wherein blood pressure is measured at a point over radial artery T. Referring to FIG. 3A through FIG. 3E, first, when the power switch 10 of the blood pressure measuring portion 2 is turned on, the pulse sensor 8 and indicating lamp 6b are connected via the pulse detecting circuit. Then, the holder pipe 3 is held by fingers and the blood pressure measuring portion 2 is positioned on the skin surface at the wrist as shown in FIG. 3A. The blood pressure measuring portion 2 is pressed by a forefinger toward the skin to allow the elastic portion 7 to abut against the skin surface.

Figure 3B:
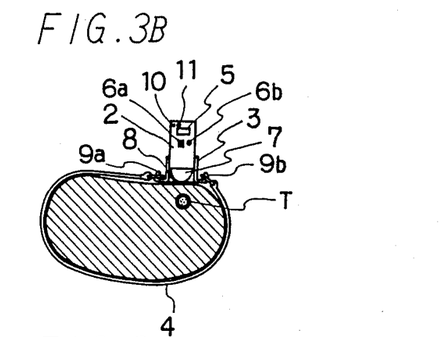

Thus the elastic portion 7 is pressed on the skin surface, and the location of radial artery T is detected by the pulse sensor 8 mounted externally on the elastic portion 7. By virtue of the function of the pulse sensor 8, the indication lamp 6b goes on and off changing the brightness thereof in accordance with the intensity of the pulse. When the location of radial artery T is detected, the brightness of the indicating lamp 6b reaches the maximum. Then, the end of the strap 4 is engaged with the strap engaging portion 9b, and the blood pressure measuring apparatus 1 is fixed at the decided position as shown in FIG. 3B.

Figure 3C:
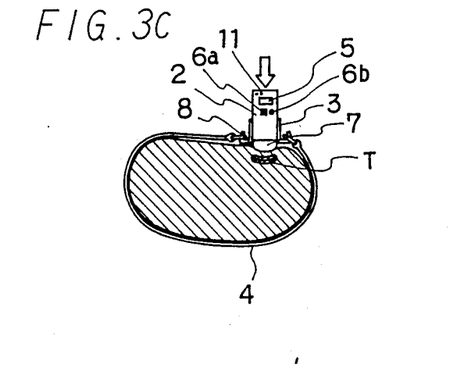

Next, the change-over switch 11 is operated so that the Korotkoff sounds detecting circuit is selected instead of the pulse detecting circuit and the pressure sensor and electronic tone generator 6a are connected via the Korotkoff sounds detecting circuit. Thereafter, the blood pressure measuring portion 2 is again pressed further by a forefinger toward the skin side, and radial artery T is constricted by the elastic portion 7 as shown in FIG. 3C. At this time, the elastic portion 7 is also constricted and deformed. When the blood pressure measuring portion 2 is pressed and the radial artery is compressed to provide a complete blockade of the blood stream, any indicating tone such as electronic tone, Korotkoff sounds and the like is not generated.

When the blood presure measuring portion 2 is released from being pressed by a forefinger, the elastic portion 7 expands due to the restitution force (in other words, the ability to reconstruct the original natural shape thereof by virtue of elastic recoil). When the internal air pressure lowers and becomes equal to the maximum blood pressure value, Korotkoff sounds which synchronize with the heart beat begin to be generated. The above Korotkoff sounds are detected by the pressure sensor, and an electronic tone is generated by electronic tone generator 6a with the assistance of the Korotkoff sounds detecting circuit at the same time when Korotkoff sounds are generated. In addition, the pressure of the compressed air at that moment in the elastic portion 7 is indicated as the maximum blood pressure on the measured value indicating portion 5 in a digital form.

Namely, the the sensor for pressure detection provided in the measuring portion 2 detects the internal air pressure of the constricted and deformed elastic portion 7 due to the above mentioned pressing, and the internal air pressure is indicated as the maximum blood pressure on the measured value indicating portion 5 in a digital form via the pressure detecting circuit at the same time when Korotkoff sounds are detected.

Figure 3D:
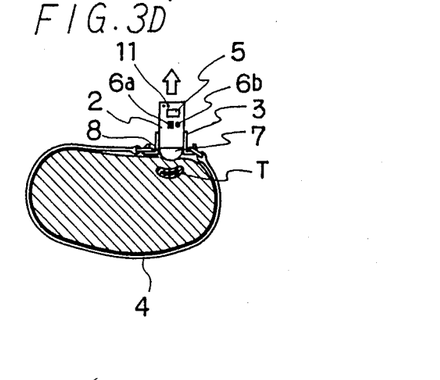
Figure 3E:
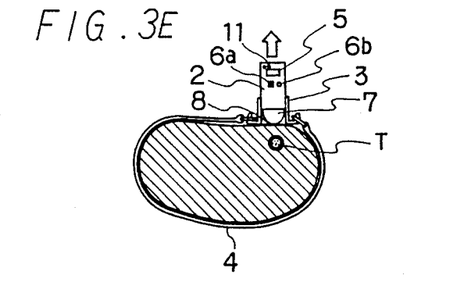

As mentioned previously, when the blood pressure measuring portion 2 is released from being pressed by a forefinger, the constricted and deformed elastic portion 7 begins to reconstruct the original shape thereof. By virtue of this restitution force of the elastic portion 7, the measuring portion 2 rises slidably in the holder pipe 3, and radial artery T which has been constricted and blocked by the elastic portion 7 is gradually released as shown in FIG. 3D. When radial artery T is released as shown in FIG. 3E and the blood pressure value becomes equal to or lower than the minimum blood pressure, the blood stream in the artery for measurement becomes a steady-state flow, and therefore Korotkoff sounds cannot be heard. When Korotkoff sounds disappear, electronic tone is generated and the blood pressure value at the time is indicated as the minimum blood pressure on the measured value indicating portion 5 in a digital form.

It should be noted than an analog-type indicator also can be used instead of or in addition to the above digital-type indicator as the measurement value indicating portions. When an analog-type indicator is used as the measured value indicating portion 5, the maximum blood pressure and the minimum blood pressure are indicated in analog form.

Thus in the course of decompression wherein the internal air pressure is reduced to 0 mm Hg, pulse sounds, namely Korotkoff sounds, are indicated during the period when the blood pressure is within a range from the maximum blood pressure to the minimum blood pressure i.e. a range of pulse pressure in a medical term. The indication of Korotkoff sounds is provided by means of generation of electronic tone and flashing of the indication lamp. Example changes in the indication in the course of depressurization of the applied pressure are as follows:

(a) Period without indication because the blood stream is completely blocked by a pressure of not lower than the maximum blood pressure.

(b) Period with indication of repeating Korotkoff sounds.

(c) Indication of the minimum blood pressure.

(d) Period without indication of Korotkoff sounds because the blood flow is returned to a steady-state flow at a pressure of not higher than the minimum blood pressure.

(e) Period until the blood pressure reaches zero.

The above indications are provided in this order.

Thus, there can be known clearly by the user the maximum blood pressure, the minimum blood pressure, the rate of pulse sounds, pulse pressure, whether or not the pulse is arrthythmic.

Figure 4:
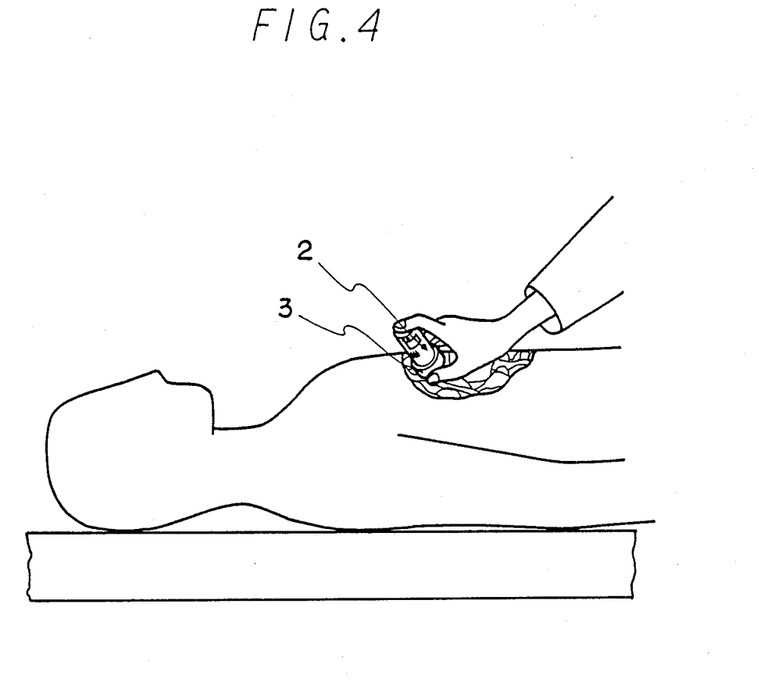
FIG. 4 is a perspective view showing a usage of an apparatus of the present invention employed for measuring blood pressure at a region other than an arm.

FIG. 4 shows an example usage of the above mentioned embodiment shown in FIG. 1 of the blood pressure measuring apparatus of the present invention when the apparatus is used for measuring at a region other than an arm. In this application, the apparatus is used without the strap 4, with the holder pipe 3 being held by a hand, and with the elastic portion 7 at the end of the blood pressure measuring portion 2 being pressed directly on an artery. By employing this manner, a blood pressure measurement at any region other than an arm is carried out using the blood pressure messureing apparatus 1.

It should be noted that the present invention is not limited to the above embodiment. The pulse sensor 8 in the above embodiment is externally mounted to the elastic portion 7, but instead of the above construction, the pulse sensor 8 can be mounted to an inner wall of the elastic portion 7 and be connected to the pulse/Korotkoff sounds detecting circuit provided in the blood pressure measuring device. Further, the design of the electronic circuit provided in the blood pressure measuring portion can be changed to any other design of the circuit as far as the maximum blood pressure detection and the minimum blood pressure detection can be carried out correctly.

As the description hereinbefore describes clearly, the apparatus of the present invention can easily find a location of an artery appropriate for blood pressure measurement by virtue of a means for searching a location of an artery appropriate for blood pressure measurement and for detecting pulse. The apparatus of the present invention can minimize a measuring error in blood pressure measurement, because the blood pressure measuring portion can be fixed to the decided appropriate point correctly and surely by fixing the holder pipe, which holds the blood pressure measuring portion, at the decided appropriate point by means of the strap.

Further, since the operation of the apparatus of the present invention is easy, the apparatus of the present invention can be easily operated even by an ordinary person, not to mention a medical doctor. Therefore, the condition of health is monitored correctly at any time in a daily life or on a journey so that a disease due to a fluctuation of blood pressure can be prevented.

Still further, the apparatus of the present invention can be used in blood pressure measurement at any region other than an arm without using the strap.

What we claim is:

1. An measuring apparatus for blood pressure comprising:
   a blood pressure measuring portion; and
   a holder pipe,
   wherein the blood pressure measuring portion includes
       a searching and detecting means for searching a location of an artery appropriate for blood pressure measurement and for detecting pulse by being pressured on a region above or near the artery, said searching and detecting means being a sensor,
       a blocking means for blocking a blood stream and being attached removably and exchangeably at one end of the blood pressure measuring portion, said blocking means being an elastic portion for pressing said region,
       a pressure detecting means for detecting blood pressure, said pressure detecting means being a sensor provided in the blood pressure measuring portion,
       a portion for indicating a measured value of blood pressure, and
       a portion for indicating a detected pulse of the appropriate artery for measurement,
   the blood pressure measuring portion being mounted slidably on the holder pipe so that an end of the blood pressure measuring portion at which the elastic portion is provided is slidably inserted in the holder pipe, the holder pipe being equipped removably with a removable strap for fixing the holder pipe and, said searching and detecting means being provided at a lower outside surface of said elastic portion such that said searching and detecting means is adapted to contact the region.

2. The apparatus according to claim 1, wherein the blood pressure measuring portion has a cylindrical shape.

3. The apparatus according to claim 1, wherein an engaging portion for engaging with the strap is provided at the outside of the holder pipe.

4. The apparatus according to claim 1, wherein the portion for indicating a measured value of blood pressure comprises a digital-type indicator.

5. The apparatus according to claim 1, wherein the elastic portion comprises a hemispheric shell made of resilient material like rubber.

6. The apparatus according to claim 5, wherein a diameter or a diagonal length of the hemispheric shell made of resilient material like rubber is not larger than 10 mm.

7. The apparatus according to claim 6, wherein a diameter or a diagonal length of the hemispheric shell made of resilient material like rubber is equal to or larger than or smaller than a diameter of a blood vessel for measurement.

8. The apparatus according to claim 5, wherein the elastic portion is formed in such a size that the one end of the blood pressure measuring portion is covered with the elastic portion.

9. The apparatus according to claim 1, wherein the elastic portion is formed in such a size that the one end of the blood pressure measuring portion is covered with the elastic portion.

10. The apparatus according to claim 1, wherein the blood pressure measuring portion has a cylindrical shape.

11. An apparatus according to claim 1, wherein said searching and detecting means is for monitoring Korotkoff sounds so than an external pressure applied to said blood pressure measuring portion is gradually reduced.

12. An apparatus according to claim 11, wherein said holder pipe is a guide means for gradually reducing external pressure applied to said blood pressure portion measuring.

13. An apparatus according to claim 1, wherein said blood pressure measuring portion has an inner wall cooperating with the blocking means to form an air-tight compartment, said searching and blocking means is mounted on the blocking means, and said pressure detecting means is mounted on the inner wall on a side facing the air-tight compartment.

* * * * *